United States Patent [19]

Miyata et al.

[11] Patent Number: 4,695,281

[45] Date of Patent: Sep. 22, 1987

[54] MEDICAL MATERIAL

[75] Inventors: Teruo Miyata, Tokyo; Yasuharu Noishiki, Tottori, both of Japan

[73] Assignee: Koken Co., Ltd., Tokyo, Japan

[21] Appl. No.: 478,773

[22] Filed: Mar. 25, 1983

[51] Int. Cl.$^4$ .......................... A61F 2/02; A61F 2/06
[52] U.S. Cl. ........................................ 623/11; 623/1; 623/16
[58] Field of Search .................. 623/18—23, 623/11, 16, 1; 128/1 R, 92 C, 92 CA, 334 R, 335 R, DIG. 21

[56] References Cited

U.S. PATENT DOCUMENTS

| | | | |
|---|---|---|---|
| 3,425,418 | 2/1969 | Chvapil et al. | 623/1 |
| 3,927,422 | 12/1975 | Sawyer | 623/1 |
| 3,955,012 | 5/1976 | Okamura et al. | 3/1 |
| 3,974,526 | 9/1976 | Dardik et al. | 3/1.4 |
| 4,349,026 | 9/1982 | Miyata | 623/1 |
| 4,466,139 | 8/1984 | Ketharanathan | 623/1 |
| 4,546,500 | 10/1985 | Bell | 623/1 |

OTHER PUBLICATIONS

Miyata et al., "Int. Healing Process of SCC Collagen Tube as an Antitrombogenic Card. Graft, Apr. 24–1982, Society Biomat.
Miyata et al., "Depositioned Platelets & Collagen or Collegen Hollow Fiber" vol. XXII Trans. Amer. Soc. Artif. Organs., 22, 261 (1976).
Noishiki et al., "Initial Healing Process of Succinylated Collagen Tube as an Antithrombogenic Cardiovascular Graft", 8th Annual Meeting of the Society for Biomaterials, Walt Disney World, Apr. 24, 27, 1982.
Sawyer et al., "Experimental and Clinical Evaluation of a New Negatively Charged Bovine Heterograft for Use in Peripheral and Coronary Revascularization", *Vascular Grafts,* Appleton-Century Crofts/New York (1978).

*Primary Examiner*—Richard J. Apley
*Assistant Examiner*—David Isabella
*Attorney, Agent, or Firm*—Armstrong, Nikaido, Marmelstein & Kubovcik

[57] ABSTRACT

The medical material according to this invention contains collagen, which as been chemically modified by saccinylation of thermal —$NH_2$ groups of said chains attached to poly peptide chains of the collagen so that the —$NH_2$ groups are converted into groups having —COOH groups. This succinylation can be carried out by reacting succinic anhydride with the —$NH_2$ groups of the collagen. Since the above medical material has excellent compatibility with living bodies, especially, with blood, it is suitable to use it as a replacement material for tissues and/or organs which are kept in contact with blood at their surfaces, namely, is suitable for use in artificial blood vessels, artificial valves, some parts of artificial hearts which are kept in contact with blood at said parts, etc. and as a patching material for hearts.

13 Claims, No Drawings

MEDICAL MATERIAL

BACKGROUND OF THE INVENTION (1) Field of the Invention

This invention relates to a medical material having excellent compatibility with living bodies, especially with blood.

(2) Brief Description of the Prior Art

Collagen is the principal component of connecting tissues of mammals, such as skins, blood vessels, bones, fasciae and teeth. It serves to protect animals from irritation from the outside and to maintain body configurations and, at the same time, it also serves as a supporting stromata for a variety of cells. Collagen accounts for one third of the whole proteins of mammals and is thus available in abundance. It has therefore found commercial utility in various industrial fields such as the leather, sausage casing and gelatin industries. In recent years, it has also come into the limelight as a medical material. Different from artificial medical materials such as synthetic polymers and ceramics, collagen makes inherently up living bodies and, corollary to this, has various characteristic properties.

(a) Due to its proteinaceous nature, it has of course antigenicity. However, its antigenicity is very weak compared with those of other proteins and its principal antigenic determinant is the telopeptido moiety which may be removed by treating collagen with a protease such as pepsin. Thus, its antigenicity can be reduced by such a pepsin treatment to such an extent that no substantial problem would occur. Its antigenicity may be reduced further by subjecting it to tanning (crosslinking) treatment using glutaraldehyde or the like.

(b) When implanted in a body, collagen is gradually allowed to substitute for a part of the connecting tissue and, as a result, absorbed in the connecting tissue. Thereafter, it is excreted as amino acids and peptides in urine. Since this absorption speed may be lowered by the tanning (crosslinking) treatment, it is possible to control the absorption speed by controlling the tanning treatment.

(c) Owing to its excellent performance as a foot step for the growth of cells, collagen has an effect to expedite the curing of a wounded part when applied thereto. It enjoys excellent compatibility with tissues in living bodies.

(d) When collagen is brought into contact with blood, it induces a platelet agglutination and subsequently development of thrombus. Therefore, it may be used as a medical material for the purpose of obtaining a hemostatic effect.

(e) Since collagen purified from bones has an activity of inducing and promoting osteogenesis, it is also used as an osteogenetic medical material for bone deficiency diseases.

As collagen has properties to cooperate with living bodies as described above, it is used as a substituent for many tissues such as bases of artificial skins, artificial blood vessels, artificial bones, hemostatics, artificial valves, patching materials, artificial tympanic membranes, and hybrid artificial organis, and as materials for contact lenses and drug carriers.

When using collagen as a blood vessel material, it is most common to chemically treat an animal blood vessel and then use the thus-treated blood vessel as an artificial blood vessel. However, collagen promotes the platelet agglutination reaction and forms thrombus when brought into contact with blood, leading to frequent occurrence of clotting of artificial blood vessels in the initial periods of implantation. However, when the formation of thrombus has occurred rather little in the initial period, the thrombus layer will be gradually absorbed and, instead, endothelia will come out from the interior of the living body and will eventually cover up the surface of the artificial blood vessel (i.e., conversion into a pseudo- and endomembrane). Once the artificial blood vessel has been covered by such a pseudo- and endomembrane, thrombus will no longer be formed and the artificial blood vessel will serve just like ordinary blood vessels. Accordingly, it is most important for a collagen-containing artificial blood vessel to minimize the development of thrombus in the initial period of implantation and to promote the conversion into a pseudo- and endomembrane.

One of the present inventors, Dr. Teruo Miyata, reported in "Deposition of Platelets and Fibrin on Chemically Modified Collagen Hollow Fiber", Trans. Amer. Soc. Artif. Int. Organs, 22, 261(1976) that the surface of succinylated collagen has anticoagulant property. Namely, hemeral venous blood was passed through a collagen capillary and the surface of the collagen capillary was observed as to adhesion and agglutination of platelets, deposition of fibrin, etc. The above observation indicated that succinylated collagen produced extremely little deposition of fibrin and far more antithrombotic compared with unsuccinylated collagen. However, it was necessary to determine if the effects of the succinylation would also be brought about in vivo as the above investigation was carried out neither in vivo nor in vitro but in-between, namely, ex-vivo.

On the other hand, another one of the present inventors, Dr. Yasuharu Noishiki, proposed a connective tissue tube making use of a "TETORON" net in "Alcohol-Preserved Homo- and Heterologus Connective Tissue Tube for Arterial Prosthesis", Artif. Organs, 2 (suppl.), 152(1977). The above connective tissue tube was formed by inserting the tube subcutaneously in an animal so that a connecting tissue consisting principally of collagen would cover all over the tube. The connective tissue tube was implanted in the thoracic descending aorta of a dog. Even shortly after the implantation (i.e., a few hours later), a thick thrombus layer having a thickness of 20–100 μm and including solid blood components entrapped therein was formed on the connective tissue tube. This thrombus was absorbed little by little and endothelia came out. This appearance of endothelia, however, took place in about 4 weeks after the implantation. Thus, the curing was very slow.

OBJECTS AND SUMMARY OF THE INVENTION

An object of this invention is to provide a medical material significantly improved in compatibility with living bodies.

Another object of this invention is to furnish a medical material which is capable of exhibiting excellent compatibility with blood and capacity of forming pseudo- and endomembranes when applied as artificial blood vessels.

A further object of this invention is to provide a medical material assuring high curing speeds.

In accordance with an aspect of this invention, the medical material contains collagen which has been chemically modified by succinylation of terminal —NH₂ groups of side chains attached to polypeptide chains of the collagen so that the —NH₂ groups are converted into groups having —COOH groups. The above medical material is thus excellent in compatibility with living bodies, for example, with blood even in living bodies, thereby being extremely effective in accelerating curing speeds.

DESCRIPTION OF THE PREFERRED EMBODIMENTS

One example of the medical material according to this invention is formed of a base, which is in turn made of such a synthetic polymer as will be described below, and succinylated collagen which covers up the base and will also be described below. The synthetic polymer may be a polyester such as "TETORON", "GOATEX" or the like. While a base made of such a synthetic polymer is kept embedded subcutaneously in an animal, the connecting tissue—which consists principally of collagen—of the animal is caused to build up to a thickness of 100 to 1,000 micrometers on the base. The above-mentioned connective tissue tube can be obtained by forming a layer of a connecting tissue on the tube made of the "TETORON" net as described above. The layer of the connecting tissue has been formed as if it fills up the meshes of the tube, which is made of the "TETORON" net" and covers up the same tube in its entirety. The tube made of the "TETORON" net, which is present in the connective tissue tube, has a thin and porous wall and thus permits capillaries to penetrate readily therethrough from the surrounding tissue. This is certainly desirous to promote the conversion of the tube into a pseudo- and endomembrane. Accordingly, the above tube is particularly suitable as a starting material for the medical material according to this invention.

Certain tissues or organs forming living bodies such as cow carotid arteries, human umbilical veins and pig ureters can also be used suitably as starting materials for medical materials according to this invention. In the case of these tissues and organs forming living bodies, it is generally necessary to carry out the succinylation of collagen contained in such organs and tissues after treating them with a protease such as trypsin or papain to remove unnecessary cell components.

The succinylation of collagen may be conducted by treating the above-mentioned artificial organs or a tissue or organ forming a living body with an acetone or alcohol solution of succinic anhydride. In the course of the treatment, certain —NH₂ groups of the polypeptide chain of collagen undergo a reaction with succinic anhydride and are converted into —NHCOCH₂CH₂COOH groups, that is, are chemically modified by groups containing —COOH groups, as shown by the following formula:

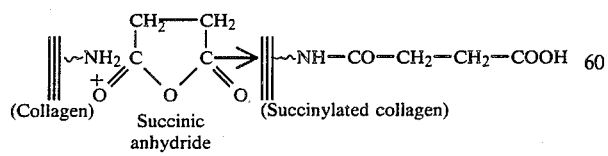

The isoionic point of collagen is lowered from about 8 to about 4.5 by the above succinylation. The succinylation renders collagen to contain more water, thereby lowering the strength of collagen. To maintain the strength of collagen, it may be possible to control the succinylation reaction and to subject only the surface area of a collagen-made medical material to succinylation so that the —NH₂ groups present inside the material would be able to take part in a tanning reaction of the material. By doing so, it is feasible to successfully carry out a tanning (crosslinking) treatment relying upon —NH₂ groups in order to make the collagen tissue physically stronger and resistant to its absorption after its implantation. The tanning (crosslinking) treatment may be carried out, for example, by reacting an aldehyde or its analogous compound such as glutaraldehyde with —NH₂ groups. Here, the percentage of succinylated —NH₂ groups to the remaining unsuccinylated —NH₂ groups may be calculated with respect to the entire collagen. Expressing the above-calculated value in terms of succinylation degree of collagen, the succinylation degree is preferably 50% or higher. Any succinylation degrees lower than 50% will not be able to bring about the effects of the succinylation to any satisfactory extent.

In artificial blood vessels made of synthetic material, for example, artificial blood vassels made of "TETORON" and artificial blood vassels made of "GOATEX", it is very effective to apply a solution of succinylated collagen on the inner walls of these artificial blood vessels for enhancing their compatibility with blood and, in view of usual network structures of these artificial blood vessels, for avoiding leakage of blood through their meshes. Medical materials which have been coated with succinylated collagen at places where they are kept in contact with blood are considered to have commercial value. The coating may be effected, for instance, by succinylating collagen which has in advance been rendered soluble with pepsin and then coating the thus-treated collagen to a thickness of 10–20 μm. Needless to say, this coating technique may similarly be applied to medical materials which have been obtained using natural tissues such as cow carotid arteries, human umbilical veins and pig ureters. Connecting tissues of animals useful for the production of medical materials should not be limited to tubular tissues such as blood vessels or ureters. The pericardium is a sheet-like membrane and is thus useful as artificial valve material, a lining material for artificial hearts (applied at places where the hearts are kept in contact with blood) and a patching material. The pericardium per se is a valuable material as it may be subjected to succinylation.

The invention will be described in further detail in the following Examples.

EXAMPLE 1

A tube having an inner diameter of 7 mm and a length of 5.7 cm was prepared with a "TETORON" net. It was kept inserted subcutaneously for 20 days in a matured dog and then taken out, with connecting tissues of the dog attached around the tube. It was thereafter treated overnight with a phosphoric acid buffer solution (pH 7.0) containing 0.01% of ficin. After washing the thus-treated tube with physiological saline, it was immersed in 500 ml of a 0.02-M borax buffer solution (pH 9.0), followed by an gradual addition of 100 ml of a 5% acetone solution of succinic anhydride while maintaining its pH always at 9 with NaOH. Subsequent to the incorporation of succinic anhydride, the resultant mixture was allowed to stand overnight at pH 9.0. Then, the thus-conditioned connective tissue tube was washed with water and then dipped in a 70% alcohol to sterilize same. After removing the alcohol with a germ-free physiological saline, the connective tissue tube was implanted in the thoracic descending aorta of a dog. It was observed for more than one month from immediately after the implantation. Unsuccinylated connective tissue tubes were also used as a control group.

The above observation was effected by eyes, optical microscope and scanning electron microscope. In the case of succinylated connective tissue tubes, no red thrombus was observed and thin layers each having a thickness in the range of 5–20 μm and consisting solely of fibrin were formed. In addition, development of endothelia was observed in one week after implantation. The growth of endothelia was fast and endothelia were allowed to spread substantially all over the surfaces of the tubes upon an elapsed time of one month, thereby completing the conversion of the tubes into pseudo- and endomembranes. Contrary to the above-mentioned succinylated connective tissue tubes, those of the control group were accompanied by the formation of thick layers of red thrombus and their conversion into pseudo- and endomembranes were delayed by 3–4 weeks. As illustrated above, succinylated connective tissue tubes are capable of avoiding thrombus formation in the initial period and permit the curing to proceed at faster speeds.

EXAMPLE 2

Surrounding adipose tissue was removed from a pig ureter and the thus-prepared pig ureter was immersed overnight in a phosphoric acid buffer solution (pH 7.0) containing 0.01% ficin. After thoroughly washing the resultant pig ureter with water, it was dipped in 500 ml of a 0.02-M borax buffer solution (pH 9.0), followed by a gradual addition of 100 ml of a 5% acetone solution of succinic anhydride while maintaining the resulting mixture always at pH 9.0 with NaOH. After holding the thus-conditioned pig ureter for 24 hours at pH 9.0, it was thoroughly washed and then sterilized with a 70% alcohol. The thus-succinylated ureter was implanted in the thoracic descending aorta of a dog. Its comparison with a control group (which had not been subjected to the succinylation treatment) showed that, in the case of the succinylated ureter, no red thrombus was formed and development of endothelia took place faster than that in the control group whereas red thrombus was formed in the initial period and conversion into pseudo- and endomembranes was delayed in the control group. It was uncovered that a succinylated ureter is an excellent material and can thus be used as an artificial blood vessel, similar to the succinylated connective tissue tube of Example 1.

EXAMPLE 3

The pericardium of a cow was washed with physiological saline and then treated overnight with a phosphoric acid buffer solution (pH 7.0) containing 0.01% of ficin. Subsequent to its washing with water, the thus-prepared pericardium was immersed in 500 ml of a borax buffer solution (0.02M; pH 9.0), followed by an addition of 100 ml of a 5% acetone solution of succinic anhydride. The resultant mixture was adjusted to pH 9.0, where the succinylation treatment was allowed to take place for 10 minutes. After washing the thus-treated pericardium with water, it was dipped in a phosphoric acid buffer solution (pH 7.4) containing 0.62% of glutaraldehyde to conduct its tanning and sterilization at the same time. The succinylation degree of the thus-prepared pericardium was 55%. Namely, 55% of all the anino groups present in the paricardium have been succinylated. Thus, the pericardium had been succinylated principally at its surfaces and its interior —NH$_2$ groups had been subjected to the tanning treatment with glutaraldehyde. Such a pericardium may be utilized for preparing artificial valves, lining artificial hearts or patching hearts. It is a material having excellent compatibility with blood and, at the same time, exhibiting sufficient strength even after its implantation in a body and undergoing no ready absorption or digestion.

EXAMPLE 4

The cow dermis was comminuted and, subsequent to its washing with a 5% salt water, washed with water, added with water to adjust the collagen concentration to about 3%, and finally adjusted to pH 3 with HCl. Pepsin was added to the thus-prepared solution in the amount of 1% based on collagen present therein. The resultant mixture was maintained at 10°–25° C. for 3–6 days, thereby causing collagen fibers to dissolve and thus obtaining a viscous collagen solution (the collagen solubilized with pepsin will hereinafter be called "atherocollagen"). By adjusting the solution to pH 7–8 with NaOH, a precipitate of atherocollagen occurred. The precipitate was collected by centrifugation and, subsequent to its washing with water, water was added thereto to give a collagen concentration of 1% and the pH of the resultant aqueous mixture was adjusted to pH 9.0. Then, a 5% acetone solution of succinic anhydride was added little by little with stirring to the above aqueous mixture while maintaining its pH always at 9.0 with NaOH. Use of succinic anhydride at a ratio of 0.5 relative to the dry weight of collagen will provide a succinylation degree of collagen of 85% or higher. After allowing the mixture to stand overnight at pH 9.0, it was adjusted to pH 4.5 to form a precipitate of succinylated atherocollagen. It was collected by centrifugation, washed with water and then purified. Since the isoionic point (pI) of the succinylated atherocollagen was 4.5, it precipitates at pH 4.5 but is dissolved in the acidic pH ranges lower than pH 4 and higher than pH 5.0.

Then, a 1% aqueous solution (pH 6.5–7.5) of succinylated atherocollagen was prepared and coated on an artificial blood vessel made of "TETORON". After its coating, the artificial blood vessel was dried in wind and exposed for one hour to ultraviolet rays from a 20-W germicidal ultraviolet lamp placed 10 cm apart from the blood vessel so as to induce crosslinking in the thus-coated succinylated atherocollagen. Artificial blood vessels made of a synthetic polymer and coated with succinylated collagen as described above will be free of blood leakage, show improved compatibility with blood and promote the formation of pseudo- and endomembranes thereon, thereby ensuring faster curing.

What is claimed is:

1. A medical material comprising collagen, the surface of the collagen being chemically modified by succinylation of terminal —NH$_2$ groups of side chains attached to polypeptide chains of the collagen, so that the —NH$_2$ groups on the surface of the collagen are converted to —COOH groups to a degree of at least 50%, based on the entire collagen; and the interior of the collagen being modified by crosslinking —NH$_2$ groups therein with one of an aldehyde and its analogous compound.

2. The medical material according to claim 1, wherein the collagen is succinylated only on its surface and not on its interior.

3. The medical material according to claim 1, wherein the medical material comprises a substrate and the succinylated collagen, the collagen being in a coating layer formed on the substrate.

4. The medical material according to claim 1, wherein the medical material comprises a substrate made of a synthetic polymer and a connecting tissue covering the substrate, the connective tissue comprising the succinylated collagen.

5. The medical material according to claim 4, wherein said base is formed of a tube of polyester.

6. The medical material according to claim 1, wherein the medical material is made of a natural tissue and collagen present in the natural tissue or organ is succinylated at least on the surface thereof.

7. The medical material according to claim 3, wherein the thickness of the coating layer is from 10 $\mu$m to 20 $\mu$m.

8. The medical material according to claim 1, wherein the isoionic point of the succinylated collagen is about 4.5.

9. The medical material according to claim 4, wherein the thickness of said connecting tissue is about 100 to 1,000 $\mu$m.

10. The medical material according to claim 1, wherein the succinylated collagen is obtained by reacting succinic anhydride with collagen.

11. The medical material according to claim 4, wherein the connecting tissue has been formed by subcutaneously the substrate made of the synthetic polymer in an animal.

12. The medical material according to claim 6, wherein the natural tissue is a member selected from the group consisting of a blood vessel, a ureter and a pericardium.

13. The medical material according to claim 3, wherein the substrate is made of a natural tissue.

* * * * *